(12) United States Patent
Chan et al.

(10) Patent No.: US 7,476,501 B2
(45) Date of Patent: *Jan. 13, 2009

(54) METHODS AND DEVICE FOR DNA SEQUENCING USING SURFACE ENHANCED RAMAN SCATTERING (SERS)

(75) Inventors: Selena Chan, Sunnyvale, CA (US); Xing Su, Cupertino, CA (US); Tae-Woong Koo, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 398 days.

This patent is subject to a terminal disclaimer.

(21) Appl. No.: 10/108,128

(22) Filed: Mar. 26, 2002

(65) Prior Publication Data

US 2003/0187237 A1  Oct. 2, 2003

(51) Int. Cl.
*C12Q 1/68* (2006.01)
(52) U.S. Cl. ........................................................ 435/6
(58) Field of Classification Search .................... 435/6, 435/287.2; 536/23.1; 204/164
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,800,159 A | 1/1989 | Mullis | |
| 4,962,037 A | 10/1990 | Jett et al. | |
| 5,038,853 A | 8/1991 | Callaway | |
| 5,306,403 A | 4/1994 | Vo-Dinh | |
| 5,401,511 A | 3/1995 | Margalit | |
| 5,405,747 A | 4/1995 | Jett et al. | |
| 5,405,766 A | 4/1995 | Kallury | |
| 5,603,872 A | 2/1997 | Margalit | |
| 5,610,287 A | 3/1997 | Nikiforov | |
| 5,721,102 A | 2/1998 | Vo-Dinh | |
| 5,776,674 A | 7/1998 | Ulmer | |
| 5,783,389 A | 7/1998 | Vo-Dinh | |
| 5,814,516 A | 9/1998 | Vo-Dinh | |
| 5,866,336 A | 2/1999 | Nazarenko et al. | |
| 5,867,266 A | 2/1999 | Craighead | |
| 5,904,824 A | 5/1999 | Oh | |
| 5,919,622 A | 7/1999 | Macho | |
| 5,986,076 A | 11/1999 | Rothschild | |
| 6,002,471 A | 12/1999 | Quake | |
| 6,040,191 A | 3/2000 | Grow | |
| 6,054,263 A | 4/2000 | Danssaert | |
| 6,054,495 A | 4/2000 | Markowitz | |
| 6,090,589 A | 7/2000 | Dimond | |
| 6,127,120 A | 10/2000 | Graham et al. | |
| 6,136,543 A | 10/2000 | Anazawa et al. | |
| 6,140,053 A | 10/2000 | Köster | |
| 6,149,868 A | 11/2000 | Natan et al. | |
| 6,174,677 B1 | 1/2001 | Vo-Dinh | |
| 6,180,372 B1 | 1/2001 | Franzen | |
| 6,180,415 B1 | 1/2001 | Schultz et al. | |
| 6,210,896 B1 | 4/2001 | Chan | |
| 6,214,246 B1 | 4/2001 | Craighead | |
| 6,219,137 B1 | 4/2001 | Vo-Dinh | |
| 6,225,068 B1 | 5/2001 | Wolfrum | |
| 6,263,286 B1 | 7/2001 | Gilmanshin | |
| 6,313,914 B1 | 11/2001 | Roe | |
| 6,344,272 B1 | 2/2002 | Oldenburg et al. | |
| 6,376,177 B1 | 4/2002 | Poponin | |
| 6,514,767 B1 | 2/2003 | Natan | |
| 6,608,716 B1 | 8/2003 | Safanov et al. | |
| 2002/0058273 A1 | 5/2002 | Shipwash | |
| 2003/0058799 A1 | 3/2003 | Berlin et al. | |
| 2003/0186240 A1* | 10/2003 | Su et al. ........................ 435/6 | |
| 2004/0110208 A1* | 6/2004 | Chan et al. ..................... 435/6 | |
| 2005/0003376 A1 | 1/2005 | Kneipp | |

FOREIGN PATENT DOCUMENTS

WO   WO 99/44045   *   8/1999

OTHER PUBLICATIONS

Matsuura et al. Real-time observation of a single DNA digestion by lambda exonuclease under fluorescence microscope field. Nucleic acids Research (2001) 29: e79.*
Sauer et al., Single molecule DNA sequencing in submicrometer channels: state of the art and future prospects. Journal of biotechnology (Apr. 2001) 86: 181-201.*
Molecular probes product information, Thiol reactive probes, MP 00003, ) Jul. 8, 2003.*
Nanogold labeling Reagents, Http://www.Nanoprobes.com/Labrgts.html (accessed Aug. 25, 2003).*
Chen. Advanced Materials, vol. 12, No. 3, pp. 186-189, 2000.*
Machara, N. et al., Efficient Detection of Single Molecules Eluting Off an Optically Trapped Microsphere, *Bioimaging* 6 (1998), 33-42.

(Continued)

*Primary Examiner*—Kenneth R. Horlick
*Assistant Examiner*—Cynthia B Wilder
(74) *Attorney, Agent, or Firm*—Darby & Darby, P.C.

(57) ABSTRACT

The methods and apparatus disclosed herein concern nucleic acid sequencing by enhanced Raman spectroscopy. In certain embodiments of the invention, exonuclease treatment of the nucleic acids 109 results in the release of nucleotides 110. The nucleotides may pass from a reaction chamber 101 through a microfluidic channel 102 and enter a nanochannel or microchannel 103. The nanochannel or microchannel 103 may be packed with nanoparticle 111 aggregates containing hot spots for Raman detection. As the nucleotides 110 pass through the nanoparticle 111 hot spots, they may be detected by surface enhanced Raman spectroscopy (SERS), surface enhanced resonance Raman spectroscopy (SERRS) and/or coherent anti-Stokes Raman spectroscopy (CARS). Identification of the sequence of nucleotides 110 released from the nucleic acid 109 provides the nucleic acid sequence. Other embodiments of the invention concern apparatus 100 for nucleic acid sequencing.

18 Claims, 1 Drawing Sheet

OTHER PUBLICATIONS

1997 DOE Human Genome Program Contractor-Grantee Workshop VI, pp. 23-25, Retrieved from the Internet URL: <http://www.ornl.gov/hgmis/publicat/97santa/seqtech.html.

M. Sauer, New Strategies for DNA Sequencing Using Diode Laser-Based Time-Resolved Fluorescence Detection [Retrieved on Nov. 12, 2001]. Retrieved from the Internet URL: <http://pc-cube01.pci.uni-heidelberg.de/alt/msauer/emsproject01.htm. 2 pages.

Lee and Meisel, *J. Phys. Chem.* 86:3391-3395, 1982.

Goodwin et al., 1996, *Acc. Chem. Res.* 29:607-613.

Feldheim, "Assembly of metal nanoparticle arrays using molecular bridges," The Electrochemical Society Interface, Fall, 2001, pp. 22-25.

K. Dörre et al., "Techniques for Single Molecule Sequencing," Bioimaging 5 (1997) 139-152.

B. Dubertret et al., "Single-Mismatch Detection Using Gold-Quenched Fluorescent Oligonucelotides," Nature Biotechnology, vol. 19, 2001, 365-370.

High-Throughput Electron-Beam Lithography System, Nova Scientific, Inc, pp. 1-4, Retrieved from the Internet URL: http://www.mdatechnology.net/techsearch.asp?articleid=510>.

Bloch et al., "Optics with an atom laser beam," *Phys. Rev. Lett.* 87, 2001.

Ivanisevic et al., "'Dip-Pen' Nanolithography on Semiconductor Surfaces," *J. Am. Chem. Soc.*, 123: 7887-7889, 2001.

Siegel, "Ion Beam Lithography," VLSI Electronics, Microstructure Science, vol. 16, Einspruch and Watts eds., Academic Press, New York, 1987.

Jin et al., "Photoinduced Conversion of Silver Nanospheres to Nanoprisms," Science, 294: 1901-1903, 2001.

Anderson et al. (2000). "Fabrication of Topologically Complex Three-Dimensional Microfluidic Systems in PDMS by Rapid Prototyping," *Anal. Chem.* 72:3158-3164.

Bennik et al. (1999). "Single-Molecule Manipulation of Double-Stranded DNS Using Optical Tweezers: Interaction Studies of DNA with RecA and YOYO-1," *Cytometry* 36:200-208.

Craighead (2000). "Nanoelectromechanical Systems," *Science* 290:1532-1536.

Effenhauser et al. (1994) "High-Speed Separation of Antisense Oligonucleotides on a Micromachined Capillary Electrophoresis Device," *Anal. Chem.* 66(18):2949-2953.

Goodman and Tippin (2000). "The Expanding Polymerase Universe," *Nat. Rev. Mol. Cell Biol.* 1(2):101-109.

Harrison et al. (1993). "Micromachining a Miniaturized Capillary Electrophoresis-Based Chemical Analysis," *Science* 261:895-897.

Holmstrom et al. (1993). "A Highly Sensitive and Fast Nonradioactive Method for Detection of Polymerase Chain Reaction Products," *Anal. Biochem.* 209:278-283.

Mehta et al. (1999). "Single-Molecule Biomechanics with Optical Methods," *Science* 283:1689-1695.

Mulvaney et al. (2003). "Glass-coated Analyte-tagged Nanoparticles: A New tagging System Based on *Detection* with Surface-Enhanced Raman Scattering," *Am. Chem. Soc.*

Running et al. (1990). "A Procedure for Productive Coupling of Synthetic Oligonucleotides to Polystyrene Microtiter Wells for Hybridization Capture," *BioTechniques* 8(3):276-277.

Newton et al. (1993). "The Production of PCR Products with 5' Single-Stranded Tails Using Primers That Incorporate Novel Phosphoramidite Intermediates," *Nucleic Acids Res.* 21(5):1155-1162.

Rasmussen et al. (1991). "Covalent Immobilization of DNA onto Polystyrene Microwells: The Molecules Are Only Bound at the 5' End," *Anal. Biochem.* 198:138-142.

Smith et al. (1999). "Inexpensive Optical Tweezers for Undergraduate Laboratories," *Am. J. Phys.* 67:26-35.

Walker et al. (1999). "Mechanical Manipulation of Bone and Cartilage Cells with 'Optical Tweezers'" *FEBS Lett.* 459:39-42, 1999.

Woolley and Mathies (1994). "Ultra-High-Speed DNA Fragment Separations Using Microfabricated Capillary Array Electrophoresis Chips," *Proc. Natl. Acad. Sci. USA* 91:11348-352.

Berger & Kimmel, (1987). *Guide to Molecular Cloning Techniques* Academic Press, New York, NY.

Sambrook, et al. (1989). *Molecular Cloning: A Laboratory Manual* 2nd Ed. Cold Spring Harbor Press, Cold Spring Harbor, NY.

*Nucleic Acid Chemistry Part 1* (1978).Townsend et al. (eds), Wiley-Interscience, New York, NY.

Vo-Dinh, Tuan. (1998). "Surface-enhanced Raman Spectroscopy Using Metallic Nanostructures," *Trac, Trends in Analytical Chemistry, Analytical Chemistry*, Cambridge, Great Britain 17(8-9):557-582.

Kneipp, K. et al. (1998). "Detection and Identification of a Single DNA Base Molecule Using Surface-enhanced Raman Scattering (SERS)," Physical Review E. Statistical Physics, Plasmas, Fluids, and Related Interdisciplinary Topics, American Institute of Physics 57(6):R6281-RT6284.

Stephan et al. (2001). "Towards a General Procedure for Sequencing Single DNA Molecules," *J. of Biotechnology* 86(3):255-267.

* cited by examiner

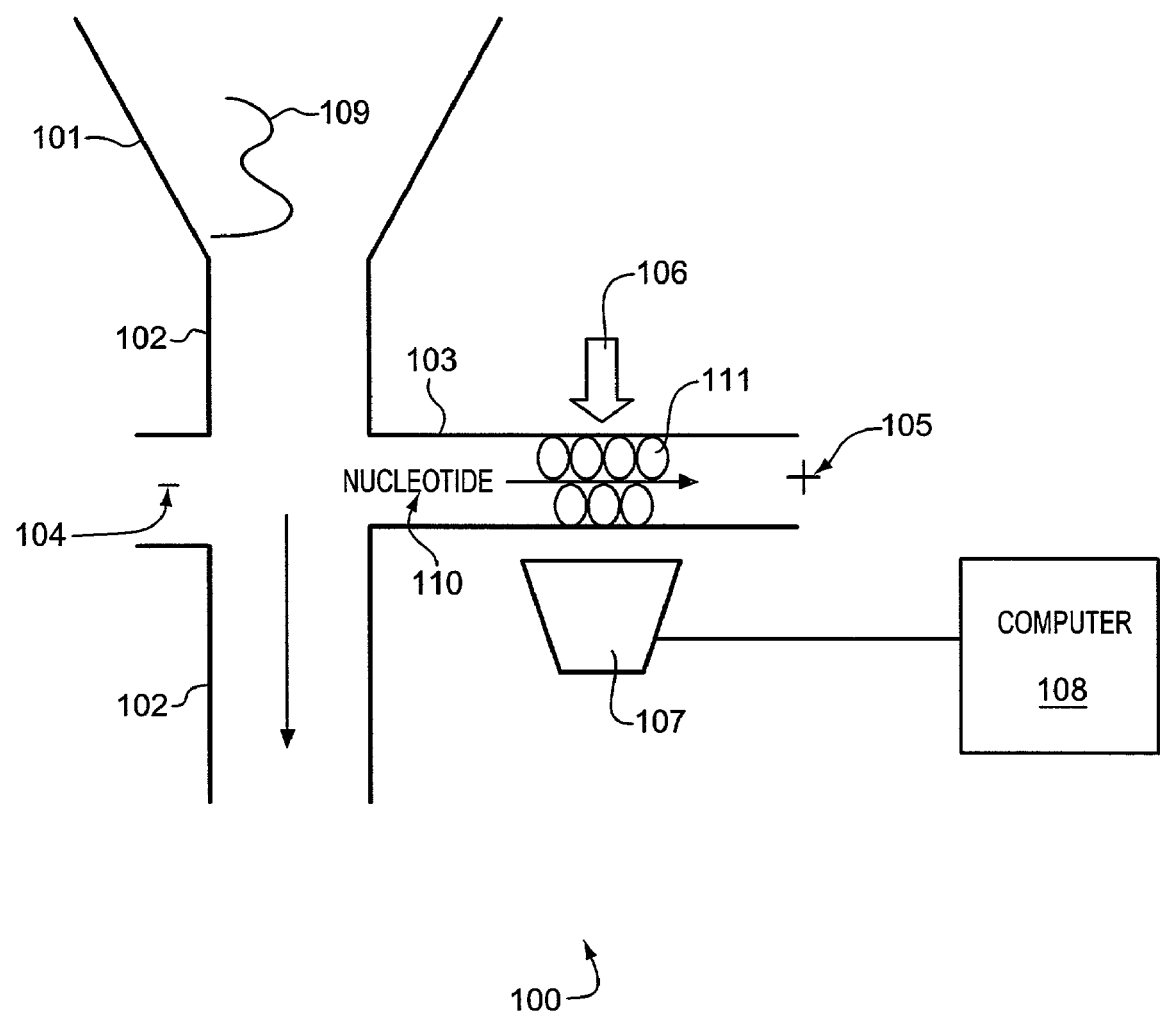

METHODS AND DEVICE FOR DNA SEQUENCING USING SURFACE ENHANCED RAMAN SCATTERING (SERS)

FIELD OF THE INVENTION

The present methods, compositions and apparatus relate to the fields of molecular biology and genomics. More particularly, the methods, compositions and apparatus concern nucleic acid sequencing using Raman spectroscopy.

BACKGROUND

Genetic information is stored in the form of very long molecules of deoxyribonucleic acid (DNA), organized into chromosomes. The human genome contains approximately three billion bases of DNA sequence. This DNA sequence information determines multiple characteristics of each individual. Many common diseases are based at least in part on variations in DNA sequence.

Determination of the entire sequence of the human genome has provided a foundation for identifying the genetic basis of such diseases. However, a great deal of work remains to be done to identify the genetic variations associated with each disease. That would require DNA sequencing of portions of chromosomes in individuals or families exhibiting each such disease, in order to identify specific changes in DNA sequence that promote the disease. Ribonucleic acid (RNA), an intermediary molecule in processing genetic information, may also be sequenced to identify the genetic bases of various diseases.

Existing methods for nucleic acid sequencing, based on detection of fluorescently labeled nucleic acids that have been separated by size, are limited by the length of the nucleic acid that can be sequenced. Typically, only 500 to 1,000 bases of nucleic acid sequence can be determined at one time. This is much shorter than the length of the functional unit of DNA, referred to as a gene, which can be tens or even hundreds of thousands of bases in length. Using current methods, determination of a complete gene sequence requires that many copies of the gene be produced, cut into overlapping fragments and sequenced, after which the overlapping DNA sequences may be assembled into the complete gene. This process is laborious, expensive, inefficient and time-consuming.

BRIEF DESCRIPTION OF THE DRAWINGS

The following drawings form part of the present specification and are included to further demonstrate certain aspects of the disclosed embodiments of the invention. The embodiments of the invention may be better understood by reference to one or more of these drawings in combination with the detailed description of specific embodiments presented herein.

FIG. 1 illustrates an exemplary apparatus 100 (not to scale) and method for nucleic acid sequencing by surface enhanced Raman spectroscopy (SERS), surface enhanced resonance Raman spectroscopy (SERRS) and/or coherent anti-Stokes Raman spectroscopy (CARS) detection.

DESCRIPTION OF ILLUSTRATIVE EMBODIMENTS

The disclosed methods, compositions and apparatus are of use for the rapid, automated sequencing of nucleic acids 109. In particular embodiments of the invention, the methods and apparatus are suitable for obtaining the sequences of very long nucleic acid molecules 109 of greater than 1,000, greater than 2,000, greater than 5,000, greater than 10,000 greater than 20,000, greater than 50,000, greater than 100,000 or even more bases in length. Advantages over prior art methods include the ability to read long nucleic acid 109 sequences in a single sequencing run, greater speed of obtaining sequence data, decreased cost of sequencing and greater efficiency in terms of the amount of operator time required per unit of sequence data.

In various embodiments of the invention, sequence information may be obtained during the course of a single sequencing run, using a single nucleic acid molecule 109. In other embodiments of the invention, multiple copies of a nucleic acid molecule 109 may be sequenced in parallel or sequentially to confirm the nucleic acid sequence or to obtain complete sequence data. In alternative embodiments of the invention, both the nucleic acid molecule 109 and its complementary strand may be sequenced to confirm the accuracy of the sequence information.

In certain embodiments of the invention, the nucleic acid 109 to be sequenced is DNA, although it is contemplated that other nucleic acids 109 comprising RNA or synthetic nucleotide analogs could be sequenced as well. The following detailed description contains numerous specific details in order to provide a more thorough understanding of the disclosed embodiments of the invention. However, it will be apparent to those skilled in the art that the embodiments of the invention may be practiced without these specific details. In other instances, devices, methods, procedures, and individual components that are well known in the art have not been described in detail herein.

In various embodiments of the invention, exemplified in FIG. 1, nucleotides 110 are sequentially removed from one or more nucleic acid molecules 109, for example by treatment with exonuclease. The nucleotides 110 exit from a reaction chamber 101 and pass into a microfluidic channel 102. The microfluidic channel 102 is in fluid communication with a channel 103, which may be a nanochannel or microchannel. In certain embodiments of the invention, nucleotides 110 enter the nanochannel or microchannel 103 in response to an electric field, negative on the microfluidic channel 102 side and positive on the nanochannel or microchannel 103 side. The electric field may be imposed, for example, through the use of negative 104 and positive 105 electrodes. As nucleotides 110 pass down the nanochannel or microchannel 103, they pass through a region of closely packed nanoparticles 111. In certain embodiments of the invention, the nanoparticles 111 may be treated to form "hot spots". Nucleotides 110 associated with a "hot spot" produce an enhanced Raman signal that may be detected using a detection unit comprising, for example, a laser 106 and CCD camera 107. Raman signals detected by the CCD camera 107 may be processed by an attached computer 108. The identity and time of passage of each nucleotide 110 through the nanoparticles 111 is recorded and used to construct the sequence of the nucleic acid 109. In some embodiments of the invention, the nucleotides 110 are unmodified. In alternative embodiments of the invention, the nucleotides 110 may be covalently modified, for example by attachment of Raman labels.

Definitions

As used herein, "a" or "an" may mean one or more than one of an item.

As used herein, "about" means within ten percent of a value. For example, "about 100" would mean a value between 90 and 110.

As used herein, a "multiplicity" of an item means two or more of the item.

As used herein, a "microchannel" is any channel with a cross-sectional diameter of between 1 micrometer ($\mu m$) and 999 $\mu m$, while a "nanochannel" is any channel with a cross-sectional diameter of between 1 nanometer (nm) and 999 nm. In certain embodiments of the invention, a "nanochannel or microchannel" may be about 1 $\mu m$ or less in diameter. A "microfluidic channel" is a channel in which liquids may move by microfluidic flow. The effects of channel diameter, fluid viscosity and flow rate on microfluidic flow are known in the art.

As used herein, "operably coupled" means that there is a functional interaction between two or more units. For example, a Raman detector 107 may be "operably coupled" to a nanochannel or microchannel 103 if the detector 107 is arranged so that it can detect analytes, such as nucleotides 110, as they pass through the nanochannel or microchannel 103.

"Nucleic acid" 109 encompasses DNA, RNA, single-stranded, double-stranded or triple stranded and any chemical modifications thereof. In certain embodiments of the invention single-stranded nucleic acids 109 are used. Virtually any modification of the nucleic acid 109 is contemplated. As used herein, a single stranded nucleic acid 109 may be denoted by the prefix "ss", a double stranded nucleic acid 109 by the prefix "ds", and a triple stranded nucleic acid 109 by the prefix "ts."

A "nucleic acid" 109 may be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule.

A "nucleoside" 110 is a molecule comprising a purine or pyrimidine base (adenine—"A", cytosine—"C", guanine—"G", thymine—"T" or uracil—"U") or any chemical modification or structural analog thereof, covalently attached to a pentose sugar such as deoxyribose or ribose or derivatives or analogs of pentose sugars.

A "nucleotide" 110 refers to a nucleoside further comprising at least one phosphate group covalently attached to the pentose sugar. In some embodiments of the invention, the nucleotides 110 to be detected are ribonucleoside monophosphates 110 or deoxyribonucleoside monophosphates 110 although in certain embodiments of the invention it is anticipated that nucleoside diphosphates or triphosphates 110 could be used. In other embodiments of the invention nucleosides 110 may be released from the nucleic acid 109 and detected. It is contemplated that various substitutions or modifications may be made in the structure of the nucleotides 110, so long as they are still capable of being released from the nucleic acid 109, for example by exonuclease activity. In certain embodiments of the invention it is contemplated that the ribose or deoxyribose moiety may be substituted with another pentose sugar or a pentose sugar analog. In other embodiments of the invention, the phosphate groups may be substituted by various analogs. In some embodiments of the invention, the purine or pyrimidine bases may be substituted or covalently modified. In embodiments of the invention involving labeled nucleotides 110, it is contemplated that the label may be attached to any portion of the nucleotide 110 so long as it does not interfere with exonuclease treatment.

Nanoparticles

Certain embodiments of the invention involve the use of nanoparticles 111 to enhance the Raman signal obtained from nucleotides 110. In some embodiments of the invention, the nanoparticles 111 are silver or gold nanoparticles 111, although any nanoparticles 111 capable of providing a surface enhanced Raman spectroscopy (SERS), surface enhanced resonance Raman spectroscopy (SERRS) and/or coherent anti-Stokes Raman spectroscopy (CARS) signal may be used. In various embodiments of the invention, nanoparticles 111 of between 1 nm and 2 $\mu m$ in diameter may be used. In alternative embodiments of the invention, nanoparticles 111 of 2 nm to 1 $\mu m$, 5 nm to 500 nm, 10 nm to 200 nm, 20 nm to 100 nm, 30 nm to 80 nm, 40 nm to 70 nm or 50 nm to 60 nm diameter are contemplated. In certain embodiments of the invention, nanoparticles 111 with an average diameter of 10 to 50 nm, 50 to 100 nm or about 100 nm are contemplated. The nanoparticles 111 may be approximately spherical in shape, although nanoparticles 111 of any shape or of irregular shape may be used. Methods of preparing nanoparticles are known (e.g., U.S. Pat. Nos. 6,054,495; 6,127,120; 6,149,868; Lee and Meisel, *J. Phys. Chem.* 86:3391-3395, 1982). Nanoparticles may also be commercially obtained (e.g., Nanoprobes Inc., Yaphank, N.Y.; Polysciences, Inc., Warrington, Pa.).

In certain embodiments of the invention, the nanoparticles 111 may be random aggregates of nanoparticles 111 (colloidal nanoparticles 111). In other embodiments of the invention, nanoparticles 111 may be cross-linked to produce particular aggregates of nanoparticles 111, such as dimers, trimers, tetramers or other aggregates. Formation of "hot spots" for SERS, SERRS and/or CARS detection may be associated with particular aggregates of nanoparticles 111. Certain alternative embodiments of the invention may use heterogeneous mixtures of aggregates of different size, while other alternative embodiments may use homogenous populations of nanoparticle aggregates 111. In certain embodiments of the invention, aggregates containing a selected number of nanoparticles 111 (dimers, trimers, etc.) may be enriched or purified by known techniques, such as ultracentrifugation in sucrose solutions. In various embodiments of the invention, nanoparticle 111 aggregates of about 100, 200, 300, 400, 500, 600, 700, 800, 900 to 1000 nm in size or larger are contemplated. In particular embodiments of the invention, nanoparticle 111 aggregates may be between about 100 nm and about 200 nm in size.

Methods of cross-linking nanoparticles 111 are known in the art (see, e.g., Feldheim, "Assembly of metal nanoparticle arrays using molecular bridges," The Electrochemical Society Interface, Fall, 2001, pp. 22-25). Reaction of gold nanoparticles 111 with linker compounds bearing terminal thiol or sulfhydryl groups is known (Feldheim, 2001). In some embodiments of the invention, a single linker compound may be derivatized with thiol groups at both ends. Upon reaction with gold nanoparticles 111, the linker would form nanoparticle 111 dimers that are separated by the length of the linker. In other embodiments of the invention, linkers with three, four or more thiol groups may be used to simultaneously attach to multiple nanoparticles 111 (Feldheim, 2001). The use of an excess of nanoparticles 111 to linker compounds prevents formation of multiple cross-links and nanoparticle 111 precipitation. Aggregates of silver nanoparticles 111 may be formed by standard synthesis methods known in the art.

Alternatively, the linker compounds used may contain a single reactive group, such as a thiol group. Nanoparticles 111 containing a single attached linker compound may self-aggregate into dimers, for example, by non-covalent interaction of linker compounds attached to two different nanoparticles 111. For example, the linker compound may comprise alkane thiols. Following attachment of the thiol group to gold nanoparticles 111, the alkane groups will tend to associate by hydrophobic interaction. In other alternative embodiments of the invention, the linker compounds may contain different functional groups at either end. For example, a linker compound could contain a sulfhydryl group at one end to allow attachment to gold nanoparticles, and a different reactive group at the other end to allow attachment to other linker compounds. Many such reactive groups are known in the art and may be used in the present methods and apparatus.

In particular embodiments of the invention, gold or silver nanoparticles 111 may be coated with derivatized silanes, such as aminosilane, 3-glycidoxypropyltrimethoxysilane (GOP) or aminopropyltrimethoxysilane (APTS). The reactive groups at the ends of the silanes may be used to form cross-linked aggregates of nanoparticles 111. It is contemplated that the linker compounds used may be of almost any length, ranging from about 0.05, 0.1, 0.2, 0.5, 0.75, 1, 2, 3, 4, 5, 6, 7, 8, 9, 10, 11, 12, 13, 14, 15, 16, 17, 18, 19, 20, 21, 22, 23, 24, 25, 27, 30, 35, 40, 45, 50, 55, 60, 65, 70, 80, 90 to 100 nm or even greater length. Certain embodiments of the invention may use linkers of heterogeneous length.

In another alternative embodiment of the invention, the nanoparticles 111 may be modified to contain various reactive groups before they are attached to linker compounds. Modified nanoparticles 111 are commercially available, such as the Nanogold® nanoparticles 111 from Nanoprobes, Inc. (Yaphank, N.Y.). Nanogold® nanoparticles 111 may be obtained with either single or multiple maleimide, amine or other groups attached per nanoparticle. The Nanogold® nanoparticles 111 are also available in either positively or negatively charged form to facilitate manipulation of nanoparticles 111 in an electric field. Such modified nanoparticles 111 may be attached to a variety of known linker compounds to provide dimers, trimers or other aggregates of nanoparticles 111.

The type of linker compound used is not limiting, so long as it results in the production of small aggregates of nanoparticles 111 that will not precipitate in solution. In some embodiments of the invention, the linker group may comprise phenylacetylene polymers (Feldheim, 2001). Alternatively, linker groups may comprise polytetrafluoroethylene, polyvinyl pyrrolidone, polystyrene, polypropylene, polyacrylamide, polyethylene or other known polymers. The linker compounds of use are not limited to polymers, but may also include other types of molecules such as silanes, alkanes, derivatized silanes or derivatized alkanes. In particular embodiments of the invention, linker compounds of relatively simple chemical structure, such as alkanes or silanes, may be used to avoid interfering with the Raman signals emitted by nucleotides 110.

In certain embodiments of the invention where the nanoparticles 111 are packed into a nanochannel or microchannel 103, the nanoparticle 111 aggregates may be manipulated into the channel 103 by any method known in the art, such as microfluidics or nanofluidics, hydrodynamic focusing or electro-osmosis. In some embodiments of the invention, use of charged linker compounds or charged nanoparticles 111 may facilitate packing of nanoparticles 111 into a channel 103 through the use of electrical gradients.

Channels, Reaction Chambers and Integrated Chips

Materials

In various embodiments of the invention, the reaction chamber 101, microfluidic channel 102, nanochannel or microchannel 103 and other components of the apparatus may be formed as a single unit, for example in the form of a chip as known in semiconductor chips and/or microcapillary or microfluidic chips. Any materials known for use in such chips may be used in the disclosed apparatus, including silicon, silicon dioxide, silicon nitride, polydimethyl siloxane (PDMS), polymethylmethacrylate (PMMA), plastic, glass, quartz, etc. In certain embodiments of the invention, part or all of the apparatus may be selected to be transparent to electromagnetic radiation at the excitation and emission frequencies used for Raman spectroscopy, such as glass, silicon, quartz or any other optically clear material. For fluid-filled compartments that may be exposed to nucleic acids and/or nucleotides, such as the reaction chamber 101, microfluidic channel 102 and nanochannel or microchannel 103, the surfaces exposed to such molecules may be modified by coating, for example to transform a surface from a hydrophobic to a hydrophilic surface and/or to decrease adsorption of molecules to a surface. Surface modification of common chip materials such as glass, silicon and/or quartz is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other coating known in the art.

Integrated Chip Manufacture

In certain embodiments of the invention, it is contemplated that the channel 103 will have a diameter between about 3 nm and about 1 µm. In particular embodiments of the invention, the diameter of the channel 103 may be selected to be slightly smaller in size than an excitatory laser beam. Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching; Methods for manufacture of nanoelectromechanical systems may be used for certain embodiments of the invention. (See, e.g., Craighead, Science 290:1532-36, 2000.) Microfabricated chips are commercially available from sources such as Caliper Technologies Inc. (Mountain View, Calif.) and ACLARA BioSciences Inc. (Mountain View, Calif.).

Microfluidic Channels and Microchannels

In certain embodiments of the invention, nucleotides 110 released from one or more nucleic acid molecules 109 are moved down a microfluidic channel 102 and then into a channel 103, which may be a nanochannel or microchannel. The microfluidic channel 102 and/or channel 103 may comprise a microcapillary (available, e.g., from ACLARA BioSciences Inc., Mountain View, Calif.) or a liquid integrated circuit (e.g., Caliper Technologies Inc., Mountain View, Calif.). Such microfluidic platforms require only nanoliter volumes of sample. In some embodiments of the invention, the nucleotides 110 may move down the microfluidic channel 102 by bulk flow of solvent. A non-limiting example of techniques for transport of nucleotides 110 includes microfluidic techniques.

In other embodiments of the invention, microcapillary electrophoresis may be used to transport nucleotides 110 down the microfluidic channel 102 and/or into the nanochannel or microchannel 103. Microcapillary electrophoresis generally involves the use of a thin capillary or channel that may or may not be filled with a particular separation medium. Electrophoresis of appropriately charged molecular species, such as negatively charged nucleotides 110, occurs in response to an imposed electrical field. Although electrophoresis is often used for size separation of a mixture of components that are simultaneously added to a microcapillary, it can also be used to transport similarly sized nucleotides 110 that are sequentially released from a nucleic acid molecule 109. Because the purine nucleotides (A, G) 110 are larger than the pyrimidine nucleotides (C, T, U) 110 and would therefore migrate more slowly, the length of the various channels 102, 103 and corresponding transit time past the detector 107 may be kept to a minimum to prevent differential migration from mixing up the order of nucleotides 110 released from the nucleic acid 109. Alternatively, the separation medium filling the microcapillary may be selected so that the migration rates of purine and pyrimidine nucleotides 110 are similar or identical. Methods of microcapillary electrophoresis have been disclosed, for example, by Woolley and Mathies (*Proc. Natl. Acad. Sci. USA* 91:11348-352, 1994).

Microfabrication of microfluidic devices, including microcapillary electrophoretic devices has been discussed in, e.g., Jacobsen et al (*Anal*. Biochem, 209:278-283,1994); Effenhauser et al. (*Anal. Chem.* 66:2949-2953, 1994); Harrison et al. (Science 261:895-897, 1993) and U.S. Pat. No. 5,904,824. Typically, these methods comprise photolithographic etching of micron scale channels on silica, silicon or other crystalline substrates or chips, and can be readily adapted for use in the disclosed methods and apparatus 100. Smaller diameter channels, such as nanochannels 103, may be prepared by known methods, such as coating the inside of a microchannel 103 to narrow the diameter, or using nanolithography, focused electron beam, focused ion beam or focused atom laser techniques. To facilitate detection of nucleotides 110, the material comprising the nanochannel or microchannel 103 may be selected to be transparent to electromagnetic radiation at the excitation and emission frequencies used. Glass, silicon, and any other materials that are generally transparent in the frequency ranges used for Raman spectroscopy may be used. In some embodiments, the nanochannel or microchannel 103 may be fabricated from the same materials used for fabrication of the reaction chamber 101 using injection molding or other known techniques.

Nanochannels

Fabrication of nanochannels 103 may utilize any technique known in the art for nanoscale manufacturing. The following techniques are exemplary only. Nanochannels 103 may be made, for example, using a high-throughput electron-beam lithography system. (http://www.mdatechnology.net/techsearch.asp?articleid=510) Electron beam lithography may be used to write features as small as 5 nm on silicon chips. Sensitive resists, such as polymethyl-methacrylate, coated on silicon surfaces may be patterned without use of a mask. The electron beam array may combine a field emitter cluster with a microchannel amplifier to increase the stability of the electron beam, allowing operation at low currents. In some embodiments of the invention, the SoftMask™ computer control system may be used to control electron beam lithography of nanoscale features on a silicon or other chip.

In alternative embodiments of the invention, nanochannels 103 may be produced using focused atom lasers. (e.g., Bloch et al., "Optics with an atom laser beam," *Phys. Rev. Lett.* 87:123-321, 2001.) Focused atom lasers may be used for lithography, much like standard lasers or focused electron beams. Such techniques are capable of producing micron scale or even nanoscale structures on a chip. In other alternative embodiments of the invention, dip-pen nanolithography may be used to form nanochannels 103. (e.g., Ivanisevic et al., "'Dip-Pen' Nanolithography on Semiconductor Surfaces," *J. Am. Chem. Soc.*, 123:7887-7889, 2001.) Dip-pen nanolithography uses atomic force microscopy to deposit molecules on surfaces, such as silicon chips. Features as small as 15 nm in size may be formed, with spatial resolution of 10 nm. Nanoscale channels 103 may be formed by using dip-pen nanolithography in combination with regular photolithography techniques. For example, a micron scale line in a layer of resist may be formed by standard photolithography. Using dip-pen nanolithography, the width of the line (and the corresponding diameter of the channel 103 after etching) may be narrowed by depositing additional resist compound on the edges of the resist. After etching of the thinner line, a nanoscale channel 103 may be formed. Alternatively, atomic force microscopy may be used to remove photoresist to form nanometer scale features.

In other alternative embodiments of the invention, ion-beam lithography may be used to create nanochannels 103 on a chip. (e.g., Siegel, "Ion Beam Lithography," VLSI Electronics, Microstructure Science, Vol. 16, Einspruch and Watts eds., Academic Press, New York, 1987.) A finely focused ion beam may be used to directly write features, such as nanochannels 103, on a layer of resist without use of a mask. Alternatively, broad ion beams may be used in combination with masks to form features as small as 100 nm in scale. Chemical etching, for example with hydrofluoric acid, is used to remove exposed silicon that is not protected by resist. The skilled artisan will realize that the techniques disclosed above are not limiting, and that nanochannels 103 may be formed by any method known in the art.

Reaction Chamber

The reaction chamber 101 is designed to hold the nucleic acid molecule 109 and exonuclease in an aqueous environment. In certain embodiments, the reaction chamber 101 may also hold an immobilization surface to which nucleic acid molecules 109 may be attached. In some embodiments of the invention, the reaction chamber 101 is designed to be temperature controlled, for example by incorporation of Pelletier elements or other methods known in the art. Methods of controlling temperature for low volume liquids are known in the art. (See, e.g., U.S. Pat. Nos. 5,038,853, 5,919,622, 6,054, 263 and 6,180,372.) In various embodiments, the reaction chamber 101 may have an internal volume of about 1, 2, 5, 10, 20, 50, 100, 250, 500 or 750 picoliters, about 1, 2, 5, 10, 20, 50, 100, 250, 500 or 750 nanoliters, about 1, 2, 5, 10, 20, 50, 100, 250, 500 or 750 microliters, or about 1 milliliter. Reaction chambers may be manufactured using known chip technologies as discussed above.

Nucleic Acids

Nucleic acid molecules 109 to be sequenced may be prepared by any technique known in the art. In certain embodiments of the invention, the nucleic acids 109 are naturally occurring DNA or RNA molecules. Virtually any naturally occurring nucleic acid 109 may be prepared and sequenced by the disclosed methods including, without limit, chromosomal, mitochondrial and chloroplast DNA and ribosomal, transfer, heterogeneous nuclear and messenger RNA. Methods for preparing and isolating various forms of cellular nucleic acids 109 are known. (See, e.g., *Guide to Molecular Cloning Techniques*, eds. Berger and Kimmel, Academic Press, New York, N.Y., 1987; *Molecular Cloning: A Labora-*

*tory Manual,* 2nd Ed., eds. Sambrook, Fritsch and Maniatis, Cold Spring Harbor Press, Cold Spring Harbor, N.Y., 1989). The methods disclosed in the cited references are exemplary only and any variation known in the art may be used. In cases where single stranded DNA (ssDNA) 109 is to be sequenced, an ssDNA 109 may be prepared from double stranded DNA (dsDNA) by any known method. Such methods may involve heating dsDNA and allowing the strands to separate, or may alternatively involve preparation of ssDNA 109 from dsDNA by known amplification or replication methods, such as cloning into M13. Any such known method may be used to prepare ssDNA or ssRNA 109.

Although certain embodiments of the invention concern analysis of naturally occurring nucleic acids 109, virtually any type of nucleic acid 109 that can serve as a substrate for an exonuclease or the equivalent could be used. For example, nucleic acids 109 prepared by various amplification techniques, such as polymerase chain reaction (PCR™) amplification, could be sequenced. (See U.S. Pat. Nos. 4,683,195, 4,683,202 and 4,800,159.) Nucleic acids 109 to be sequenced may alternatively be cloned in standard vectors, such as plasmids, cosmids, BACs (bacterial artificial chromosomes) or YACs (yeast artificial chromosomes). (See, e.g., Berger and Kimmel, 1987; Sambrook et al., 1989.) Nucleic acid inserts 109 may be isolated from vector DNA, for example, by excision with appropriate restriction endonucleases, followed by agarose gel electrophoresis. Methods for isolation of insert nucleic acids 109 are known in the art.

Isolation of Single Nucleic Acid Molecules

In certain embodiments of the invention, the nucleic acid molecule 109 to be sequenced is a single molecule of ssDNA or ssRNA. A variety of methods for selection and manipulation of single ssDNA or ssRNA molecules 109 may be used, for example, hydrodynamic focusing, micro-manipulator coupling, optical trapping, or a combination of these and similar methods. (See, e.g., Goodwin et al., 1996, *Acc. Chem. Res.* 29:607-619; U.S. Pat. Nos. 4,962,037; 5,405,747; 5,776,674; 6,136,543; 6,225,068.)

In certain embodiments of the invention, microfluidics or nanofluidics may be used to sort and isolate nucleic acid molecules 109. Hydrodynamics may be used to manipulate the movement of nucleic acids 109 into a microchannel, microcapillary, or a micropore. In one embodiment, hydrodynamic forces may be used to move nucleic acid molecules 109 across a comb structure to separate single nucleic acid molecules 109. Once the nucleic acid molecules 109 have been separated, hydrodynamic focusing may be used to position the molecules 109 within a reaction chamber 101. A thermal or electric potential, pressure or vacuum can also be used to provide a motive force for manipulation of nucleic acids 109. In exemplary embodiments of the invention, manipulation of nucleic acids 109 for sequencing may involve the use of a channel block design incorporating microfabricated channels and an integrated gel material, as disclosed in U.S. Pat. Nos. 5,867,266 and 6,214,246.

In another embodiment, a sample containing the nucleic acid molecule 109 may be diluted prior to coupling to an immobilization surface. In exemplary embodiments of the invention, the immobilization surface may be in the form of magnetic or non-magnetic beads or other discrete structural units. At an appropriate dilution, each bead will have a statistical probability of binding zero or one nucleic acid molecule 109. Beads with one attached nucleic acid molecule 109 may be identified using, for example, fluorescent dyes and flow cytometer sorting or magnetic sorting. Depending on the relative sizes and uniformity of the beads and the nucleic acids 109, it may be possible to use a magnetic filter and mass separation to separate beads containing a single bound nucleic acid molecule 109. In other embodiments of the invention, multiple nucleic acids 109 attached to a single bead or other immobilization surface may be sequenced.

In alternative embodiments of the invention, a coated fiber tip may be used to generate single molecule nucleic acids 109 for sequencing (e.g., U.S. Pat. No. 6,225,068). In other alternative embodiments of the invention, the immobilization surfaces may be prepared to contain a single molecule of avidin or other cross-linking agent. Such a surface could attach a single biotinylated nucleic acid molecule 109 to be sequenced. This embodiment is not limited to the avidin-biotin binding system, but may be adapted to any coupling system known in the art.

In other alternative embodiments of the invention, an optical trap may be used for manipulation of single molecule nucleic acid molecules 109 for sequencing. (E.g., U.S. Pat. No. 5,776,674). Exemplary optical trapping systems are commercially available from Cell Robotics, Inc. (Albuquerque, N. Mex.), S+L GmbH (Heidelberg, Germany) and P.A.L.M. Gmbh (Wolfratshausen, Germany).

Methods of Immobilization

In various embodiments of the invention, the nucleic acid molecules 109 to be sequenced may be attached to a solid surface (or immobilized). Immobilization of nucleic acid molecules 109 may be achieved by a variety of methods involving either non-covalent or covalent attachment between the nucleic acid molecule 109 and the surface. In an exemplary embodiment, immobilization may be achieved by coating a surface with streptavidin or avidin and the subsequent attachment of a biotinylated nucleic acid 109 (Holmstrom et al., *Anal. Biochem.* 209:278-283, 1993). Immobilization may also occur by coating a silicon, glass or other surface with poly-L-Lys (lysine) or poly L-Lys, Phe (phenylalanine), followed by covalent attachment of either amino- or sulfhydryl-modified nucleic acids 109 using bifunctional crosslinking reagents (Running et al., *BioTechniques* 8:276-277, 1990; Newton et al., *Nucleic Acids Res.* 21:1155-62, 1993). Amine residues may be introduced onto a surface through the use of aminosilane for cross-linking.

Immobilization may take place by direct covalent attachment of 5'-phosphorylated nucleic acids 109 to chemically modified surfaces (Rasmussen et al., *Anal. Biochem.* 198: 138-142, 1991). The covalent bond between the nucleic acid 109 and the surface is formed by condensation with a water-soluble carbodiimide. This method facilitates a predominantly 5'-attachment of the nucleic acids 109 via their 5'-phosphates.

DNA 109 is commonly bound to glass by first silanizing the glass surface, then activating with carbodiimide or glutaraldehyde. Alternative procedures may use reagents such as 3-glycidoxypropyltrimethoxysilane (GOP) or aminopropyltrimethoxysilane (APTS) with DNA 109 linked via amino linkers incorporated either at the 3' or 5' end of the molecule. DNA 109 may be bound directly to membrane surfaces using ultraviolet radiation. Other non-limiting examples of immobilization techniques for nucleic acids 109 are disclosed in U.S. Pat. Nos. 5,610,287, 5,776,674 and 6,225,068.

The type of surface to be used for immobilization of the nucleic acid 109 is not limiting. In various embodiments of the invention, the immobilization surface may be magnetic beads, non-magnetic beads, a planar surface, a pointed surface, or any other conformation of solid surface comprising almost any material, so long as the material is sufficiently durable and inert to allow the nucleic acid 109 sequencing reaction to occur. Non-limiting examples of surfaces that may be used include glass, silica, silicate, PDMS, silver or other metal coated surfaces, nitrocellulose, nylon, activated quartz, activated glass, polyvinylidene difluoride (PVDF), polystyrene, polyacrylamide, other polymers such as poly(vinyl chloride), poly(methyl methacrylate) or poly(dimethyl siloxane), and photopolymers which contain photoreactive species such as nitrenes, carbenes and ketyl radicals capable of forming covalent links with nucleic acid molecules 109 (See U.S. Pat. Nos. 5,405,766 and 5,986,076).

Bifunctional cross-linking reagents may be of use in various embodiments of the invention, such as attaching a nucleic acid molecule 109 to a surface. The bifunctional crosslinking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for crosslinking molecules are disclosed in U.S. Pat. Nos. 5,603,872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

Exonuclease

In certain embodiments of the invention, methods of nucleic acid sequencing may involve binding of an exonuclease to the free end of a nucleic acid molecule 109 and removal of nucleotides 110 one at a time. The embodiments of the invention are not limited by the type of exonuclease that may be used. Non-limiting examples of exonucleases of potential use include *E. coli* exonuclease I, III, V or VII, Bal 31 exonuclease, mung bean exonuclease, S1 nuclease, *E. coli* DNA polymerase I holoenzyme or Klenow fragment, RecJ, exonuclease T, T4 or T7 DNA polymerase, Taq polymerase, exonuclease T7 gene 6, snake venom phosphodiesterase, spleen phosphodiesterase, *Thermococcus litoralis* DNA polymerase, *Pyrococcus* sp. GB-D DNA polymerase, lambda exonuclease, *S. aureus* micrococcal nuclease, DNase I, ribonuclease A, T1 micrococcal nuclease, or other exonucleases known in the art. Exonucleases are available from commercial sources such as New England Biolabs (Beverly, Mass.), Amersham Pharmacia Biotech (Piscataway, N.J.), Promega (Madison, Wis.), Sigma Chemicals (St. Louis, Mo.) or Boehringer Mannheim (Indianapolis, Ind.).

The skilled artisan will realize that enzymes with exonuclease activity have various properties known in the art. The rate of exonuclease activity may be manipulated to coincide with the optimal rate of analysis of nucleotides 110 by the detector 107. Various methods are known for adjusting the rate of exonuclease activity, including adjusting the temperature, pressure, pH, salt concentration or divalent cation concentration in the reaction chamber 101. Methods of optimization of exonuclease activity are known in the art.

Raman Labels

Certain embodiments of the invention may involve attaching a label to the nucleotides 110 to facilitate their measurement by the Raman detector 107. Non-limiting examples of labels that could be used for Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins and aminoacridine. These and other Raman labels may be obtained from commercial sources (e.g., Molecular Probes, Eugene, Oreg.).

Polycyclic aromatic compounds in general may function as Raman labels, as is known in the art. Other labels that may be of use for particular embodiments of the invention include cyanide, thiol, chlorine, bromine, methyl, phosphorus and sulfur. In certain embodiments of the invention, carbon nanotubes may be of use as Raman labels. The use of labels in Raman spectroscopy is known (e.g., U.S. Pat. Nos. 5,306,403 and 6,174,677). The skilled artisan will realize that Raman labels should generate distinguishable Raman spectra when bound to different types of nucleotide 110.

Labels may be attached directly to the nucleotides 110 or may be attached via various linker compounds. Alternatively, nucleotide precursors that are covalently attached to Raman labels are available from standard commercial sources (e.g., Roche Molecular Biochemicals, Indianapolis, Ind.; Promega Corp., Madison, Wis.; Ambion, Inc., Austin, Tex.; Amersham Pharmacia Biotech, Piscataway, N.J.). Raman labels that contain reactive groups designed to covalently react with other molecules, such as nucleotides 110, are commercially available (e.g., Molecular Probes, Eugene, Oreg.). Methods for preparing labeled nucleotides 110 and incorporating them into nucleic acids 109 are known (e.g., U.S. Pat. Nos. 4,962, 037; 5,405,747; 6,136,543; 6,210,896).

Detection Unit

In some embodiments of the invention, the detection unit is designed to detect and quantify nucleotides 110 by Raman spectroscopy. Various methods for detection of nucleotides 110 by Raman spectroscopy are known in the art. (See, e.g., U.S. Pat. Nos. 5,306,403; 6,002,471; 6,174,677). Variations on surface enhanced Raman spectroscopy (SERS), surface enhanced resonance Raman spectroscopy (SERRS) and coherent anti-Stokes Raman spectroscopy (CARS) have been disclosed. In SERS and SERRS, the sensitivity of the Raman detection is enhanced by a factor of $10^6$ or more for molecules adsorbed on roughened metal surfaces, such as silver, gold, platinum, copper or aluminum surfaces.

A non-limiting example of a Raman detection unit is disclosed in U.S. Pat. No. 6,002,471. In this embodiment of the invention, the excitation beam is generated by either a Nd:YAG laser 106 at 532 nm wavelength or a Ti:sapphire laser 106 at 365 nm wavelength. Pulsed laser beams or continuous laser beams may be used. The excitation beam passes through confocal optics and a microscope objective, and is focused onto the nanochannel or microchannel 103 containing packed nanoparticles 111. The Raman emission light from the nucleotides 110 is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector 107. The detector 107 includes an avalanche photodiode interfaced with a computer for counting and digitization of the signal.

Alternative examples of detection units are disclosed, for example, in U.S. Pat. No. 5,306,403, including a Spex Model 1403 double-grating spectrophotometer 107 equipped with a gallium-arsenide photomultiplier tube (RCA Model C31034 or Burle Industries Model C3103402) operated in the single-photon counting mode. The excitation source 106 is a 514.5 nm line argon-ion laser 106 from SpectraPhysics, Model 166, and a 647.1 nm line of a krypton-ion laser 106 (Innova 70, Coherent).

Alternative excitation sources 106 include a nitrogen laser 106 (Laser Science Inc.) at 337 nm and a helium-cadmium laser 106 (Liconox) at 325 nm (U.S. Pat. No. 6,174,677). The excitation beam may be spectrally purified with a bandpass filter (Corion) and may be focused on a nanochannel or microchannel 103 using a 6× objective lens (Newport, Model L6X). The objective lens may be used to both excite the nucleotides 110 and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors 107 include an ISA HR-320 spectrograph equipped with a red-enhanced intensified charge-coupled device (REICCD) detection system (Princeton Instruments). Other types of detectors 107 may be used, such as charged injection devices, photodiode arrays or phototransistor arrays.

Any suitable form or configuration of Raman spectroscopy or related techniques known in the art may be used for detection of nucleotides 110, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

Information Processing and Control System and Data Analysis

In certain embodiments of the invention, the nucleic acid sequencing apparatus 100 may comprise an information processing system. The embodiments are not limiting for the type of information processing system used. An exemplary information processing system may incorporate a computer comprising a bus for communicating information and a processor for processing information. In one embodiment, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, or a Pentium Xeon® processor (Intel Corp., Santa Clara, Calif.). In various other embodiments of the invention, the processor may be based on Intel® architecture, such as Intel® IA-32 or Intel® IA-64 architecture. Alternatively, other processors may be used.

The computer may further comprise a random access memory (RAM) or other dynamic storage device, a read only memory (ROM) or other static storage and a data storage device such as a magnetic disk or optical disc and its corresponding drive. The information processing system may also comprise other peripheral devices known in the art, such as a display device (e.g., cathode ray tube or Liquid Crystal Display), an alphanumeric input device (e.g., keyboard), a cursor control device (e.g., mouse, trackball, or cursor direction keys) and a communication device (e.g., modem, network interface card, or interface device used for coupling to Ethernet, token ring, or other types of networks).

In particular embodiments of the invention, the detection unit may be operably coupled to the information processing system. Data from the detection unit may be processed by the processor and data stored in the main memory. Data on emission profiles for standard nucleotides 110 may also be stored in main memory or in ROM. The processor may compare the emission spectra from nucleotides 110 in the nanochannel or microchannel 103 to identify the type of nucleotide 110 released from the nucleic acid molecule 109. The main memory may also store the sequence of nucleotides 110 released from the nucleic acid molecule 109. The processor may analyze the data from the detection unit to determine the sequence of the nucleic acid 109. It is appreciated that a differently equipped information processing system may be used for certain implementations. Therefore, the configuration of the system may vary in different embodiments of the invention.

While the processes described herein may be performed under the control of a programmed processor, in alternative embodiments of the invention, the processes may be fully or partially implemented by any programmable or hardcoded logic, such as Field Programmable Gate Arrays (FPGAs), TTL logic, or Application Specific Integrated Circuits (ASICs), for example. Additionally, the disclosed methods may be performed by any combination of programmed general purpose computer components and/or custom hardware components.

Following the data gathering operation, the data will typically be reported to a data analysis operation. To facilitate the analysis operation, the data obtained by the detection unit will typically be analyzed using a digital computer such as that described above. Typically, the computer will be appropriately programmed for receipt and storage of the data from the detection unit as well as for analysis and reporting of the data gathered.

In certain embodiments of the invention, custom designed software packages may be used to analyze the data obtained from the detection unit. In alternative embodiments of the invention, data analysis may be performed, using an information processing system and publicly available software packages. Non-limiting examples of available software for DNA sequence analysis include the PRISM™ DNA Sequencing Analysis Software (Applied Biosystems, Foster City, Calif.), the Sequencher™ package (Gene Codes, Ann Arbor, Mich.), and a variety of software packages available through the National Biotechnology Information Facility at website www.nbif.org/links/1.4.1.php.

EXAMPLES

Example 1

Nucleic Acid Sequencing Using Raman Detection and Nanoparticles

Certain embodiments of the invention, exemplified in FIG. 1, involve sequencing of one or more single-stranded nucleic acid molecules 109 that may be attached to an immobilization surface in a reaction chamber 101. In such embodiments of the invention, the reaction chamber 101 contains one or more exonucleases that sequentially remove one nucleotide 110 at a time from the unattached end of the nucleic acid molecule.

As the nucleotides 110 are released, they move down a microfluidic channel 102 and then into a nanochannel or microchannel 103, past a detection unit. The detection unit comprises an excitation source 106, such as a laser, that emits an excitatory beam. The excitatory beam interacts with the released nucleotides 110 so that electrons are excited to a higher energy state. The Raman emission spectrum that results from the return of the electrons to a lower energy state is detected by a Raman spectroscopic detector 107, such as a spectrometer, a monochromator or a charge coupled device (CCD), such as a CCD camera.

The excitation source 106 and detector 107 are arranged so that nucleotides 110 are excited and detected as they pass through a region of closely packed nanoparticles 111 in the nanochannel or microchannel 103. The nanoparticles 111 may be cross-linked to form "hot spots" for Raman detection. By passing the nucleotides 110 through the nanoparticle 111 hot spots, the sensitivity of Raman detection is increased by many orders of magnitude.

Preparation of Reaction Chamber, Microfluidic Channel and Microchannel

Borofloat glass wafers (Precision Glass & Optics, Santa Ana, Calif.) are pre-etched for a short period in concentrated HF (hydrofluoric acid) and cleaned before deposition of an amorphous silicon sacrificial layer in a plasma-enhanced chemical vapor deposition (PECVD) system (PEII-A, Technics West, San Jose, Calif.). Wafers are primed with hexamethyldisilazane (HMDS), spin-coated with photoresist (Shipley 1818, Marlborough, Mass.) and soft-baked. A contact mask aligner (Quintel Corp. San Jose, Calif.) is used to expose the photoresist layer with one or more mask designs, and the exposed photoresist removed using a mixture of Microposit developer concentrate (Shipley) and water. Developed wafers are hard-baked and the exposed amorphous silicon removed using $CF_4$ (carbon tetrafluoride) plasma in a PECVD reactor. Wafers are chemically etched with concentrated HF to produce the reaction chamber 101, microfluidic channel 102 and microchannel 103. The remaining photoresist is stripped and the amorphous silicon removed.

Nanochannels 103 are formed by a variation of this protocol. Standard photolithography as described above is used to form the micron scale features of the integrated chip. A thin layer of resist is coated onto the chip. An atomic force microscopy/scanning tunneling probe tip is used to remove a 5 to 10 nm wide strip of resist from the chip surface. The chip is briefly etched with dilute HF to produce a nanometer scale groove on the chip surface. In the present non-limiting example, a channel 103 with a diameter of between 500 nm and 1 μm is prepared.

Access holes are drilled into the etched wafers with a diamond drill bit (Crystalite, Westerville, Ohio). A finished chip is prepared by thermally bonding two complementary etched and drilled plates to each other in a programmable vacuum furnace (Centurion VPM, J. M. Ney, Yucaipa, Calif.). Alternative exemplary methods for fabrication of a chip incorporating a reaction chamber 101, microfluidic channel 102 and nanochannel or microchannel 103 are disclosed in U.S. Pat. Nos. 5,867,266 and 6,214,246. In certain embodiments of the invention, a nylon filter with a molecular weight cutoff of 2,500 daltons is inserted between the reaction chamber 101 and the microfluidic channel 102 to prevent exonuclease 15 from leaving the reaction chamber 101.

Nanoparticle Preparation

Silver nanoparticles 111 are prepared according to Lee and Meisel (*J. Phys. Chem.* 86:3391-3395, 1982). Gold nanoparticles 111 are purchased from Polysciences, Inc. (Warrington, Pa.) or from Nanoprobes, Inc. (Yaphank, N.Y.). Gold nanoparticles 111 are available from Polysciences, Inc. in 5, 10, 15, 20, 40 and 60 nm sizes and from Nanoprobes, Inc. in 1.4 nm size. In the present non-limiting Example, 60 nm gold nanoparticles 111 are used.

Gold nanoparticles 111 are reacted with alkane dithiols, with chain lengths ranging from 5 nm to 50 nm. The linker compounds contain thiol groups at both ends of the alkane to react with gold nanoparticles 111. An excess of nanoparticles 111 to linker compounds is used and the linker compounds are slowly added to the nanoparticles 111 to avoid formation of large nanoparticle aggregates. After incubation for two hours at room temperature, nanoparticle 111 aggregates are separated from single nanoparticles 111 by ultracentrifugation in 1 M sucrose. Electron microscopy reveals that aggregates prepared by this method contain from two to six nanoparticles 111 per aggregate. The aggregated nanoparticles 111 are loaded into the microchannel 103 by microfluidic flow. A constriction at the far end of the microchannel 103 holds the nanoparticle aggregates 111 in place.

Nucleic Acid Preparation and Exonuclease Treatment

Human chromosomal DNA is purified according to Sambrook et al. (1989). Following digestion with Bam H1, the genomic DNA fragments are inserted into the multiple cloning site of the pBluescript® II phagemid vector (Stratagene, Inc., La Jolla, Calif.) and grown up in *E. coli*. After plating on ampicillin-containing agarose plates a single colony is selected and grown up for sequencing. Single-stranded DNA copies of the genomic DNA insert are rescued by co-infection with helper phage. After digestion in a solution of proteinase K:sodium dodecyl sulphate (SDS), the DNA is phenol extracted and then precipitated by addition of sodium acetate (pH 6.5, about 0.3 M) and 0.8 volumes of 2-propanol. The DNA containing pellet is resuspended in Tris-EDTA buffer and stored at −20° C. until use. Agarose gel electrophoresis shows a single band of purified DNA.

M13 forward primers complementary to the known pBluescript® sequence, located next to the genomic DNA insert, are purchased from Midland Certified Reagent Company (Midland, Tex.). The primers are covalently modified to contain a biotin moiety attached to the 5' end of the oligonucleotide. The biotin group is covalently linked to the 5'-phosphate of the primer via a $(CH_2)_6$ spacer. Biotin-labeled primers are allowed to hybridize to the ssDNA template molecules prepared from the pBluescript® vector. The primer-template complexes are then attached to streptavidine coated beads according to Dorre et al. (Bioimaging 5: 139-152, 1997). At appropriate DNA dilutions, a single primer-template complex is attached to a single bead. A bead containing a single primer-template complex is inserted into the reaction chamber 101 of a sequencing apparatus 100.

The primer-template is incubated with modified T7 DNA polymerase (United States Biochemical Corp., Cleveland, Ohio). The reaction mixture contains unlabeled deoxyadenosine-5'-triphosphate (dATP) and deoxyguanosine-5'-triphosphate (dGTP), digoxigenin-labeled deoxyuridine-5'-triphosphate (digoxigenin-dUTP) and rhodamine-labeled deoxycytidine-5'-triphosphate (rhodamine-dCTP). The polymerization reaction is allowed to proceed for 2 hours at 37° C. After synthesis of the digoxigenin and rhodamine labeled nucleic acid 109, the template strand is separated from the labeled nucleic acid 109, and the template strand, DNA polymerase and unincorporated nucleotides are washed out of the reaction chamber 101. In alternative embodiments of the invention, all deoxynucleoside triphosphates used for polymerization are unlabeled. In other alternative embodiments, single stranded nucleic acids 109 may be directly sequenced without polymerization of a complementary strand.

Exonuclease activity is initiated by addition of exonuclease III to the reaction chamber 101. The reaction mixture is maintained at pH 8.0 and 37° C. As nucleotides 110 are released from the 3' end of the nucleic acid 109, they are transported by microfluidic flow down the microfluidic channel 102. At the entrance to the microchannel 103, an electrical potential gradient created by the electrodes 104, 105 drives the nucleotides 110 out of the microfluidic channel 102 and into the microchannel 103. As the nucleotides 110 pass through the packed nanoparticles 111, they are exposed to excitatory radiation from a laser 106. Raman emission spectra is detected by the Raman detector 107 as disclosed below.

Raman Detection of Nucleotides

The detection unit comprises a laser 106 and Raman detector 107. The excitation beam is generated by a titanium:sapphire laser 106 (Tsunami by Spectra-Physics) at a near-infrared wavelength (750~950 nm) or a galium aluminum arsenide diode laser 106 (PI-ECL series by Process Instruments) at 785 nm or 830 nm. Pulsed laser beams or continuous beams may be used. The excitation beam is reflected by a dichroic mirror (holographic notch filter by Kaiser Optical or an interference filter by Chroma or Omega Optical) into a collinear geometry with the collected beam. The reflected beam passes a microscope objective (Nikon LU series), and is focused onto the microchannel 103 where target nucleotides 110 are located. The Raman scattered light from the target nucleotides 110 is collected by the same microscope objective, and passes the dichroic mirror to the Raman detector 107. The Raman detector 107 comprises a focusing lens, a spectrograph, and an array detector. The focusing lens focuses the Raman scattered light through the entrance slit of the spectrograph. The spectrograph (RoperScientific) comprises a grating that disperses the light by its wavelength. The dispersed light is imaged onto an array detector (back-illuminated deep-depletion CCD camera by RoperScientific). The array detector is connected to a controller circuit, which is connected to a computer for data transfer and control of the detector 107 function.

The Raman detector 107 is capable of detecting and identifying single nucleotides 110 of dATP, dGTP, rhodamine-dCTP and digoxigenin-dUTP moving past the detector 107. Data on the time course for labeled nucleotide detection is compiled and analyzed to obtain the sequence of the nucleic acid 109. In alternative embodiments, the detector 107 is capable of detecting and identifying single unlabeled nucleotides.

All of the METHODS and APPARATUS disclosed and claimed herein can be made and used without undue experimentation in light of the present disclosure. It will be apparent to those of skill in the art that variations may be applied to the METHODS and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. A method of identifying a single nucleotide by Raman spectroscopy, comprising:

contacting a nucleic acid molecule attached at one end to a immobilization surface with one or more exonucleases to remove the single nucleotide from an unattached end of the nucleic acid molecule;

separating the single nucleotide from the immobilized nucleic acid, transferring the single nucleotide to a hot spot comprising a plurality of cross-linked nanoparticle aggregates packed within a microfluidic channel, wherein association of the single nucleotide with the hot spot enhances Raman signaling; and identifying the single nucleotide by Raman spectroscopy.

2. The method of claim 1, wherein the single nucleotide is removed from the nucleic acid by exonuclease activity.

3. The method of claim 1, wherein the plurality of nanoparticle aggregates comprises between two to six nanoparticles per aggregate.

4. The method of claim 1, wherein said nucleic acid is immobilized in a reaction chamber.

5. The method of claim 4, wherein a single nucleic acid is immobilized in said reaction chamber.

6. The method of claim 1, wherein said the single nucleotide is identified by surface enhanced Raman spectroscopy (SERS), surface enhanced resonance Raman spectroscopy (SERRS) and/or coherent anti-Stokes Raman spectroscopy (CARS).

7. The method of claim 1, wherein said channel is a nanochannel or microchannel.

8. The method of claim 3, wherein the plurality of nanoparticle aggregates comprises two nanoparticles per aggregate.

9. The method of claim 3, wherein the nanoparticles comprise gold and/or silver, said nanoparticles between about 1 nm and 2 μm in size.

10. The method of claim 9, wherein the size of said nanoparticles is selected from the group consisting of about 10 to 50 nm, about 50 to 100 nm, about 10 to 100 nm, about 100 nm and about 200 nm.

11. The method of claim 8, wherein the surfaces of said nanoparticles are covalently modified with organic compounds.

12. The method of claim 1, further comprising:

attaching the nucleic acid molecule to the immobilization surface.

13. The method of claim 1, further comprising imposing an electric field to move the single nucleotide through said channel.

14. The method of claim 1, further comprising recording the time at which the single nucleotide passes through said channel.

15. The method of claim 1, wherein the single nucleotide produces a unique Raman signal.

16. The method of claim 1, wherein at least a portion of the nucleic acid molecule comprises a single stranded nucleic acid.

17. The method of claim 1, wherein the single nucleotide is a single unlabeled nucleotide.

18. The method of claim 1, wherein the single nucleotide is a single Raman labeled nucleotide.

* * * * *